(12) United States Patent
Bonutti

(10) Patent No.: US 11,013,602 B2
(45) Date of Patent: May 25, 2021

(54) SCAFFOLD FOR ALLOPROSTHETIC COMPOSITE IMPLANT

(71) Applicant: Mako Surgical Corp., Fort Lauderdale, FL (US)

(72) Inventor: Peter M. Bonutti, Manalapan, FL (US)

(73) Assignee: Mako Surgical Corp., Fort Lauderdale, FL (US)

( * ) Notice: Subject to any disclaimer, the term of this patent is extended or adjusted under 35 U.S.C. 154(b) by 0 days.

(21) Appl. No.: 15/635,373

(22) Filed: Jun. 28, 2017

(65) Prior Publication Data

US 2018/0008418 A1 Jan. 11, 2018

Related U.S. Application Data

(60) Provisional application No. 62/359,809, filed on Jul. 8, 2016.

(51) Int. Cl.
*A61F 2/28* (2006.01)
*A61L 27/36* (2006.01)
(Continued)

(52) U.S. Cl.
CPC ........ *A61F 2/30767* (2013.01); *A61B 5/4509* (2013.01); *A61B 17/1635* (2013.01);
(Continued)

(58) Field of Classification Search
CPC .......... A61F 2002/3092; A61F 2/30767; A61F 2/30942; A61F 2002/30141;
(Continued)

(56) References Cited

U.S. PATENT DOCUMENTS

| 4,192,021 | A | 3/1980 | Deibig et al. |
| 4,608,199 | A | 8/1986 | Caplan et al. |

(Continued)

FOREIGN PATENT DOCUMENTS

| EP | 1689330 A1 | 8/2006 |
| JP | 6149950 | 3/1986 |

(Continued)

OTHER PUBLICATIONS

Extended European Search Report for EP17180110 dated Mar. 26, 2018.

(Continued)

*Primary Examiner* — Ann Schillinger
(74) *Attorney, Agent, or Firm* — Lerner, David, Littenberg, Krumholz & Mentlik, LLP

(57) ABSTRACT

An alloprosthetic composite implant comprising includes a structural porous scaffold having a pore density profile corresponding to a density profile of bone to be replaced. A plurality of cells are seeded within pores of the porous scaffold and grown by incubation. The cells may include osteoblasts and/or stem cells to form the structure of the implant, and one or more cartilage layers may be grown on top of the scaffold. The pore density profile of the scaffold may be formed based on one or both of the bone density profile of the bone to be removed, and the bone density profile of the native bone that will be in contact with the alloprosthetic implant. A robot may be employed reo resect the native bone and also to shape the alloprosthetic implant to fit into place in the native bone.

17 Claims, 9 Drawing Sheets

(51) Int. Cl.
  *A61B 17/15* (2006.01)
  *A61F 2/30* (2006.01)
  *A61B 34/30* (2016.01)
  *A61B 5/00* (2006.01)
  *A61B 17/16* (2006.01)
  *A61L 27/04* (2006.01)
  *A61L 27/24* (2006.01)
  *A61L 27/38* (2006.01)
  *A61L 27/56* (2006.01)
  *A61B 34/10* (2016.01)
  *A61F 2/46* (2006.01)

(52) U.S. Cl.
  CPC ............... *A61B 34/30* (2016.02); *A61F 2/28* (2013.01); *A61F 2/30756* (2013.01); *A61F 2/30942* (2013.01); *A61L 27/04* (2013.01); *A61L 27/24* (2013.01); *A61L 27/3612* (2013.01); *A61L 27/3821* (2013.01); *A61L 27/56* (2013.01); *A61B 2034/108* (2016.02); *A61F 2002/30011* (2013.01); *A61F 2002/3092* (2013.01); *A61F 2002/30762* (2013.01); *A61F 2002/30929* (2013.01); *A61F 2002/30952* (2013.01); *A61F 2002/30962* (2013.01); *A61F 2002/30985* (2013.01); *A61F 2002/4633* (2013.01); *A61F 2002/4648* (2013.01); *A61F 2310/00011* (2013.01); *A61F 2310/00359* (2013.01); *A61F 2310/00371* (2013.01); *A61F 2310/00964* (2013.01); *A61L 2430/24* (2013.01)

(58) Field of Classification Search
  CPC .. A61F 2002/30144; A61F 2002/30148; A61F 2002/30151; A61F 2002/30154; A61F 2002/30273; A61F 2002/30331; A61F 2002/3093; A61F 2002/30146; A61F 2002/30153; A61B 17/00234; A61B 17/68; A61B 17/866; A61B 2017/00526; A61B 17/56; A61B 5/4509; A61B 5/4836; A61B 5/686
  See application file for complete search history.

(56) References Cited

U.S. PATENT DOCUMENTS

| | | |
|---|---|---|
| 4,609,551 A | 9/1986 | Caplan et al. |
| 4,663,720 A | 5/1987 | Duret et al. |
| 4,742,464 A | 5/1988 | Duret et al. |
| 4,936,862 A | 6/1990 | Walker et al. |
| 5,150,304 A | 9/1992 | Berchem et al. |
| 5,197,985 A | 3/1993 | Caplan et al. |
| 5,226,914 A | 7/1993 | Caplan et al. |
| 5,257,203 A | 10/1993 | Riley et al. |
| 5,273,964 A | 12/1993 | Lemons |
| 5,274,565 A | 12/1993 | Reuben |
| 5,365,996 A | 11/1994 | Crook |
| 5,448,489 A | 9/1995 | Reuben |
| 5,452,407 A | 9/1995 | Crook |
| 5,486,359 A | 1/1996 | Caplan et al. |
| 5,514,137 A | 5/1996 | Coutts |
| 5,556,429 A | 9/1996 | Felt |
| 5,607,469 A | 3/1997 | Frey |
| 5,755,809 A | 5/1998 | Cohen et al. |
| 5,824,084 A | 10/1998 | Muschler |
| 5,880,964 A | 3/1999 | Schall et al. |
| 5,902,825 A | 5/1999 | Jia |
| 6,049,026 A | 4/2000 | Muschler |
| 6,112,109 A | 8/2000 | D'Urso |
| 6,140,452 A | 10/2000 | Felt et al. |
| 6,177,151 B1 | 1/2001 | Chrisey et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,254,639 B1 | 7/2001 | Peckitt |
| 6,280,474 B1 | 8/2001 | Cassidy et al. |
| 6,306,177 B1 | 10/2001 | Felt et al. |
| 6,319,712 B1 | 11/2001 | Meenen et al. |
| 6,395,007 B1 | 5/2002 | Bhatnagar et al. |
| 6,527,810 B2 | 3/2003 | Johnson et al. |
| 6,564,083 B2 | 5/2003 | Stevens |
| 6,572,572 B2 | 6/2003 | Pomatto et al. |
| 6,607,561 B2 | 8/2003 | Brannon |
| 6,613,054 B2 | 9/2003 | Scribner et al. |
| 6,632,247 B2 | 10/2003 | Boyer, II et al. |
| 6,696,073 B2 | 2/2004 | Boyce et al. |
| 6,711,432 B1 | 3/2004 | Krause et al. |
| 6,719,761 B1 | 4/2004 | Reiley et al. |
| 6,723,131 B2 | 4/2004 | Muschler |
| 6,733,747 B2 | 5/2004 | Anderson et al. |
| 6,736,799 B1 | 5/2004 | Erbe et al. |
| 6,746,451 B2 | 6/2004 | Middleton et al. |
| 6,767,354 B2 | 7/2004 | Johanson et al. |
| 6,767,369 B2 | 7/2004 | Boyer, II et al. |
| 6,776,800 B2 | 8/2004 | Boyer, II et al. |
| 6,786,930 B2 | 9/2004 | Biscup |
| 6,818,018 B1 | 11/2004 | Sawhney |
| 6,827,720 B2 | 12/2004 | Leali |
| 6,863,899 B2 | 3/2005 | Koblish et al. |
| 6,864,101 B1 | 3/2005 | Winkler et al. |
| 6,887,246 B2 | 5/2005 | Bhatnagar et al. |
| 6,932,610 B2 | 8/2005 | Ono et al. |
| 6,981,948 B2 | 1/2006 | Pellegrino et al. |
| 6,986,788 B2 | 1/2006 | Paul et al. |
| 7,018,382 B2 | 3/2006 | Merboth et al. |
| 7,045,125 B2 | 5/2006 | Erbe et al. |
| 7,050,877 B2 | 5/2006 | Iseki et al. |
| 7,052,517 B2 | 5/2006 | Murphy et al. |
| 7,063,726 B2 | 6/2006 | Crouch et al. |
| 7,087,087 B2 | 8/2006 | Boyer, II et al. |
| 7,131,605 B2 | 11/2006 | McPherson et al. |
| 7,147,846 B2 | 12/2006 | Anderson et al. |
| 7,153,307 B2 | 12/2006 | Scribner et al. |
| 7,166,570 B2 | 1/2007 | Hunter et al. |
| 7,175,336 B2 | 2/2007 | Voellmicke et al. |
| 7,261,720 B2 | 8/2007 | Stevens et al. |
| 7,291,450 B2 | 11/2007 | Sowemimo-Coker et al. |
| 7,299,805 B2 | 11/2007 | Bonutti |
| 7,300,465 B2 | 11/2007 | Paul et al. |
| 7,374,678 B2 | 5/2008 | Leach et al. |
| 7,383,094 B2 | 6/2008 | Kopelman et al. |
| 7,425,549 B2 | 9/2008 | Little et al. |
| 7,442,195 B1 | 10/2008 | Behrens |
| 7,447,556 B2 | 11/2008 | McBagonluri et al. |
| 7,462,181 B2 | 12/2008 | Kraft et al. |
| 7,470,371 B2 | 12/2008 | Dorian et al. |
| 7,483,558 B2 | 1/2009 | Greene, Jr. et al. |
| 7,621,963 B2 | 11/2009 | Simon et al. |
| 7,655,010 B2 | 2/2010 | Serhan et al. |
| 7,670,384 B2 | 3/2010 | Kumar et al. |
| 7,708,742 B2 | 5/2010 | Scribner et al. |
| 7,736,366 B2 | 6/2010 | Abdelgany et al. |
| 7,744,597 B2 | 6/2010 | Gaskins et al. |
| 7,747,305 B2 | 6/2010 | Dean et al. |
| 7,771,431 B2 | 8/2010 | Scribner et al. |
| 7,771,590 B2 | 8/2010 | Leach et al. |
| 7,776,594 B2 | 8/2010 | Bays et al. |
| 7,780,860 B2 | 8/2010 | Higgins et al. |
| 7,806,276 B2 | 10/2010 | Leach et al. |
| 7,811,290 B2 | 10/2010 | Rabiner |
| 7,819,888 B2 | 10/2010 | Johanson et al. |
| 7,831,292 B2 | 11/2010 | Quaid et al. |
| 7,832,566 B2 | 11/2010 | Leach et al. |
| 7,837,884 B2 | 11/2010 | Dorian et al. |
| 7,845,499 B2 | 12/2010 | Higgins et al. |
| 7,858,296 B2 | 12/2010 | Sowemimo-Coker et al. |
| 7,887,598 B2 | 2/2011 | Evans et al. |
| 7,892,291 B2 | 2/2011 | Evans et al. |
| 7,914,689 B2 | 3/2011 | Higgins et al. |
| 7,923,203 B2 | 4/2011 | Sowemimo-Coker et al. |
| 7,992,725 B2 | 8/2011 | Leach et al. |

(56) References Cited

U.S. PATENT DOCUMENTS

| | | |
|---|---|---|
| 7,993,578 B2 | 8/2011 | Kadiyala |
| 7,996,099 B2 | 8/2011 | Kopelman et al. |
| 8,002,733 B2 | 8/2011 | Kraft et al. |
| 8,034,014 B2 | 10/2011 | Higgins et al. |
| 8,043,253 B2 | 10/2011 | Kraft et al. |
| 8,043,377 B2 | 10/2011 | Guyer et al. |
| 8,048,297 B2 | 11/2011 | Leach et al. |
| 8,048,320 B2 | 11/2011 | Leach et al. |
| 8,048,321 B2 | 11/2011 | Leach et al. |
| 8,060,236 B2 | 11/2011 | Hilliard |
| 8,062,364 B1 | 11/2011 | Sharkey et al. |
| 8,062,372 B2 | 11/2011 | Tsuang et al. |
| 8,062,534 B2 | 11/2011 | Higgins et al. |
| 8,086,336 B2 | 12/2011 | Christensen |
| 8,109,919 B2 | 2/2012 | Kraft et al. |
| 8,116,900 B2 | 2/2012 | Slemker et al. |
| 8,119,013 B2 | 2/2012 | Leach et al. |
| 8,137,408 B2 | 3/2012 | Kadiyala et al. |
| 8,147,500 B2 | 4/2012 | Beyar et al. |
| 8,152,813 B2 | 4/2012 | Osorio et al. |
| 8,160,345 B2 | 4/2012 | Pavlovskaia et al. |
| 8,163,032 B2 | 4/2012 | Evans et al. |
| 8,163,184 B2 | 4/2012 | Leach et al. |
| 8,168,692 B2 | 5/2012 | Wenz |
| 8,183,042 B2 | 5/2012 | Liao et al. |
| 8,187,477 B2 | 5/2012 | Dorian et al. |
| 8,187,556 B2 | 5/2012 | Kadiyala |
| 8,200,355 B2 | 6/2012 | Lee et al. |
| 8,221,430 B2 | 7/2012 | Park et al. |
| 8,236,258 B2 | 8/2012 | Leach et al. |
| 8,287,522 B2 | 10/2012 | Moses et al. |
| 8,287,915 B2 | 10/2012 | Clineff et al. |
| 8,303,967 B2 | 11/2012 | Clineff et al. |
| 8,303,976 B2 | 11/2012 | Sapieszko et al. |
| 8,308,340 B2 | 11/2012 | Ferrante et al. |
| 8,313,742 B2 | 11/2012 | Kadiyala et al. |
| 8,313,954 B2 | 11/2012 | Leach et al. |
| 8,328,024 B2 | 12/2012 | Leach et al. |
| 8,337,711 B2 | 12/2012 | Dorian et al. |
| 8,419,802 B2 | 4/2013 | Evans et al. |
| 8,425,619 B2 | 4/2013 | Evans et al. |
| 8,435,306 B2 | 5/2013 | Evans et al. |
| 8,455,254 B2 | 6/2013 | Tsai et al. |
| 8,460,686 B2 | 6/2013 | Clineff et al. |
| 8,483,863 B1 | 7/2013 | Knox |
| 8,497,236 B2 | 7/2013 | Benedict et al. |
| 8,512,575 B2 | 8/2013 | Leach et al. |
| 8,551,178 B2 | 10/2013 | Sharkey et al. |
| 8,567,609 B2 | 10/2013 | Landrigan et al. |
| 8,591,391 B2 | 11/2013 | Chavarria et al. |
| 8,596,470 B2 | 12/2013 | Leach et al. |
| 8,603,346 B2 | 12/2013 | Leach et al. |
| 8,613,938 B2 | 12/2013 | Akella et al. |
| 8,617,171 B2 | 12/2013 | Park et al. |
| 8,623,094 B2 | 1/2014 | Evans et al. |
| 8,652,148 B2 | 2/2014 | Zuhars |
| 8,657,482 B2 | 2/2014 | Malackowski et al. |
| 8,663,146 B2 | 3/2014 | Higgins et al. |
| 8,685,429 B2 | 4/2014 | Koblish et al. |
| 8,690,874 B2 | 4/2014 | Thorne |
| 8,702,809 B2 | 4/2014 | Nauman et al. |
| 8,715,353 B2 | 5/2014 | Bagga et al. |
| 8,734,822 B2 | 5/2014 | Koblish et al. |
| 8,742,072 B2 | 6/2014 | Thorne |
| 8,783,470 B2 | 7/2014 | Hecker et al. |
| 8,801,586 B2 | 8/2014 | Dorian et al. |
| 8,808,551 B2 | 8/2014 | Leach et al. |
| 8,838,263 B2 | 9/2014 | Sivak et al. |
| 8,845,736 B2 | 9/2014 | Zhang et al. |
| 8,876,911 B2 | 11/2014 | Murphy et al. |
| 8,882,848 B2 | 11/2014 | Sharkey et al. |
| 8,950,586 B2 | 2/2015 | Dorian et al. |
| 8,992,703 B2 | 3/2015 | O'Neill et al. |
| 8,992,862 B2 | 3/2015 | Leach et al. |
| 8,998,998 B2 | 4/2015 | Sharkey et al. |
| 9,011,800 B2 | 4/2015 | Leach et al. |
| 9,039,998 B2 | 5/2015 | Guillemot et al. |
| 9,045,735 B2 | 6/2015 | Muschler et al. |
| 9,056,017 B2 | 6/2015 | Kotlus |
| 2001/0033857 A1* | 10/2001 | Vyakarnam ............... A61F 2/28 424/443 |
| 2002/0007294 A1* | 1/2002 | Bradbury ............... G16H 15/00 705/2 |
| 2002/0029045 A1* | 3/2002 | Bonutti ............... A61B 17/0401 606/86 R |
| 2002/0183417 A1 | 12/2002 | Shimp |
| 2003/0039676 A1 | 2/2003 | Boyce et al. |
| 2003/0055316 A1 | 3/2003 | Brannon |
| 2003/0055431 A1 | 3/2003 | Brannon |
| 2003/0109784 A1 | 6/2003 | Loh et al. |
| 2003/0114936 A1 | 6/2003 | Sherwood et al. |
| 2003/0135214 A1 | 7/2003 | Fetto et al. |
| 2003/0138473 A1 | 7/2003 | Koblish et al. |
| 2003/0157271 A1 | 8/2003 | Duignan et al. |
| 2003/0216669 A1 | 11/2003 | Lang et al. |
| 2003/0236573 A1 | 12/2003 | Evans et al. |
| 2004/0022689 A1 | 2/2004 | Wulf et al. |
| 2005/0049706 A1 | 3/2005 | Brodke et al. |
| 2005/0101673 A1 | 5/2005 | Norden et al. |
| 2005/0119219 A1 | 6/2005 | Bellini et al. |
| 2005/0251266 A1 | 11/2005 | Maspero et al. |
| 2005/0261795 A1 | 11/2005 | Ghosh et al. |
| 2005/0272153 A1 | 12/2005 | Xuenong et al. |
| 2006/0057184 A1 | 3/2006 | Nycz et al. |
| 2006/0064164 A1 | 3/2006 | Thelen et al. |
| 2006/0105015 A1 | 5/2006 | Perla et al. |
| 2006/0172934 A1 | 8/2006 | Nycz et al. |
| 2006/0282020 A1 | 12/2006 | Bertagnoli et al. |
| 2007/0010440 A1 | 1/2007 | Schense et al. |
| 2007/0113951 A1 | 5/2007 | Huang |
| 2007/0123894 A1 | 5/2007 | Claypool et al. |
| 2007/0244484 A1 | 10/2007 | Luginbuehl |
| 2007/0259018 A1 | 11/2007 | McKay |
| 2007/0264612 A1 | 11/2007 | Mount |
| 2007/0265705 A1 | 11/2007 | Gaissmaier et al. |
| 2007/0275028 A1 | 11/2007 | Barry et al. |
| 2007/0276501 A1 | 11/2007 | Betz et al. |
| 2007/0287988 A1 | 12/2007 | Trebing et al. |
| 2008/0031915 A1 | 2/2008 | Becerra Ratia et al. |
| 2008/0038487 A1 | 2/2008 | Barron et al. |
| 2008/0113008 A1 | 5/2008 | Roche |
| 2008/0249632 A1 | 10/2008 | Stone et al. |
| 2008/0294085 A1 | 11/2008 | Stamps et al. |
| 2008/0294269 A1 | 11/2008 | Fell |
| 2009/0005868 A1 | 1/2009 | Gundlapalli et al. |
| 2009/0081076 A1 | 3/2009 | Baege et al. |
| 2009/0081169 A1 | 3/2009 | Egrise et al. |
| 2009/0123378 A1 | 5/2009 | Wong et al. |
| 2009/0164014 A1 | 6/2009 | Liljensten et al. |
| 2009/0287332 A1 | 11/2009 | Adusumilli et al. |
| 2009/0292379 A1 | 11/2009 | Pitz |
| 2010/0076503 A1 | 3/2010 | Beyar et al. |
| 2010/0114351 A1 | 5/2010 | Kopelman et al. |
| 2010/0145451 A1 | 6/2010 | Dee |
| 2010/0152873 A1 | 6/2010 | Dunne et al. |
| 2010/0179549 A1 | 7/2010 | Keller et al. |
| 2010/0256692 A1 | 10/2010 | Kang et al. |
| 2010/0268363 A1 | 10/2010 | Karim et al. |
| 2011/0106093 A1 | 5/2011 | Romano et al. |
| 2011/0172611 A1 | 7/2011 | Yoo et al. |
| 2013/0060278 A1 | 3/2013 | Bozung et al. |
| 2013/0144392 A1 | 6/2013 | Hughes |
| 2013/0204384 A1* | 8/2013 | Hensley ............... A61F 2/30942 623/20.35 |
| 2013/0224278 A1* | 8/2013 | Czaja ............... C08B 15/02 424/426 |
| 2013/0267026 A1 | 10/2013 | Bonutti |
| 2013/0325142 A1* | 12/2013 | Hunter ............... C22C 1/08 623/23.51 |
| 2014/0012393 A1 | 1/2014 | Shin et al. |
| 2014/0263214 A1 | 9/2014 | Dahotre et al. |
| 2014/0336545 A1 | 11/2014 | Bonuttti |

(56) References Cited

U.S. PATENT DOCUMENTS

2014/0371897 A1    12/2014   Lin et al.
2015/0182295 A1     7/2015   Bozung et al.
2017/0172743 A1     6/2017   Bonutti

FOREIGN PATENT DOCUMENTS

| JP | 2003126124 A | 5/2003 |
| JP | 2004159982 A | 6/2004 |
| KR | 20060108961 A | 10/2006 |
| KR | 20080103389 A | 11/2008 |
| WO | 01/85040 A1 | 11/2001 |
| WO | 03056320 A2 | 7/2003 |
| WO | 2005107949 A1 | 11/2005 |
| WO | 2006026981 A1 | 3/2006 |
| WO | 2007025290 A3 | 3/2007 |
| WO | 2007139949 A2 | 12/2007 |
| WO | 2008143469 A2 | 11/2008 |
| WO | 2010102059 A1 | 9/2010 |
| WO | 2014145406 A1 | 9/2014 |

OTHER PUBLICATIONS

Partial European Search Report for EP 17 18 0110 completed Nov. 20, 2017.
Extended European Search Report for Application No. EP 19192955.3 dated Jan. 31, 2020, 5 pages.
European Search Report for Application No. EP 19192955.3, dated Mar. 11, 2021, 7 pages.

\* cited by examiner

SCAFFOLD FOR ALLOPROSTHETIC COMPOSITE IMPLANT

CROSS-REFERENCE TO RELATED APPLICATIONS

This application claims the benefit of the filing date of U.S. Provisional Patent Application No. 62/359,809 filed Jul. 8, 2016, the disclosure of which is hereby incorporated by reference herein.

BACKGROUND OF THE DISCLOSURE

Joint replacement, particularly articulating joint replacement, is a commonly performed procedure in orthopedic surgery. However, the ideal material for replacement joints remains elusive. Typically, joint reconstruction involves repair of a bony defect, articular cartilage and in some cases, other tissue such as one or more joining ligaments. For example, in a typical knee arthroplasty procedure, damaged or otherwise deficient cartilage may be removed from the patient along with a portion of subchondral bone. A prosthetic knee implant is implanted into the knee, typically with a metallic portion providing structural support and a plastic component coupled to the metallic portion to provide a bearing surface for articulation with respect to another implant or native tissue.

The goal of a joint arthroplasty is generally to restore functionality to the joint in a way that closely mimics a healthy native joint. Metal and plastic implant may have a number of benefits, for example, ease and accuracy of production. However, there is increasing interest in designing implants, articular or otherwise, that are at least partially formed of biologic components to more closely mimic the tissue being replaced.

BRIEF SUMMARY

According to a first aspect of the disclosure, an alloprosthetic composite implant for replacing a joint includes a structural porous scaffold having a pore density profile corresponding to a density profile of a bone of the joint to be replaced. A plurality of cells is seeded within pores of the porous scaffold. At least one layer of cartilage may be positioned on an end of the scaffold, the cartilage adapted to replace at least a portion of a joint surface of the joint. The density profile of the porous scaffold may include a relatively low density inner portion adapted to contact native bone of a patient, and a relatively high density outer portion opposite the inner portion. The porous scaffold may be formed from at least one of metal and collagen. The cells seeded within pores of the porous scaffold may be selected from the group consisting of stem cells and osteoblasts. The at least one layer of cartilage may include an outer gliding layer of cartilage and an inner layer of cartilage underneath the outer gliding layer. The pore density of a portion of the scaffold configured to contact a native bone of a patient may be formed to correspond to a bone density of the native bone to be contacted.

According to another aspect of the disclosure, a method of implanting an alloprosthetic composite implant includes forming a scaffold having a pore density profile, seeding a plurality of viable cells into the scaffold, incubating the scaffold including the plurality of viable cells, robotically resecting native bone of a patient, and robotically machining the alloprosthetic composite implant following incubation to have a shape corresponding to the native bone of the patient that is to be replaced. The step of forming the scaffold may be performed by additive manufacturing, such as 3-D printing. The method may also include determining a bone density profile of a bone of a patient to be replaced by the alloprosthetic composite implant. In this case, the pore density profile of the scaffold may be formed based on the determined bone density profile of the bone to be replaced. The method may additionally or alternately include determining a bone density profile of a native bone to be contacted by the alloprosthetic composite implant. In this case, a portion of the scaffold intended to contact the native bone may be formed with a pore density profile based on the determined bone density profile. The step of seeding a plurality of viable cells into the scaffold may include seeding osteoblasts and/or pluripotent cells into the scaffold. A first inner layer of cartilage may be formed on the scaffold, and a second layer of cartilage may be formed on the first layer of cartilage. The step of robotically machining the alloprosthetic composite implant may be performed intraoperatively. The step of incubating the scaffold may include incubating the scaffold in a nutrient rich medium. The step of robotically resecting native bone of the patient may include forming a first interlocking shape in the native bone and the step of robotically machining the alloprosthetic composite implant may include forming a second interlocking shape in the alloprosthetic composite having a complementary shape to the first interlocking shape.

DETAILED DESCRIPTION

Different options are available for designing a prosthetic implant. For example, implants may be formed completely of metals and/or plastics and/or other non-biologic materials. Alternatively, implants may be formed of biologic materials, which may be, for example, autografts, allografts, and/or xenografts. Such biologic implants may be harvested from a donor and implanted as harvested (or as modified following harvesting). However, when using fresh or frozen osteochondral allograft materials, it can be very difficult to get the patient's bone to grow into the surface of the allograft. Biologic implants may also be grown ex vivo. For example, attempts have been made to grow bone and cartilage for later implantation as part of a joint arthroplasty or other joint repair procedure. Other implants may attempt to combine non-biologic implants with biological components. One example of this is metallic implants that have a porous surface to allow the patient's bone to grow into the metallic portion in vivo on a first side of the implant, with a metallic or plastic bearing surface on a second side to provide an articular surface for the prosthetic joint.

Figure 1:
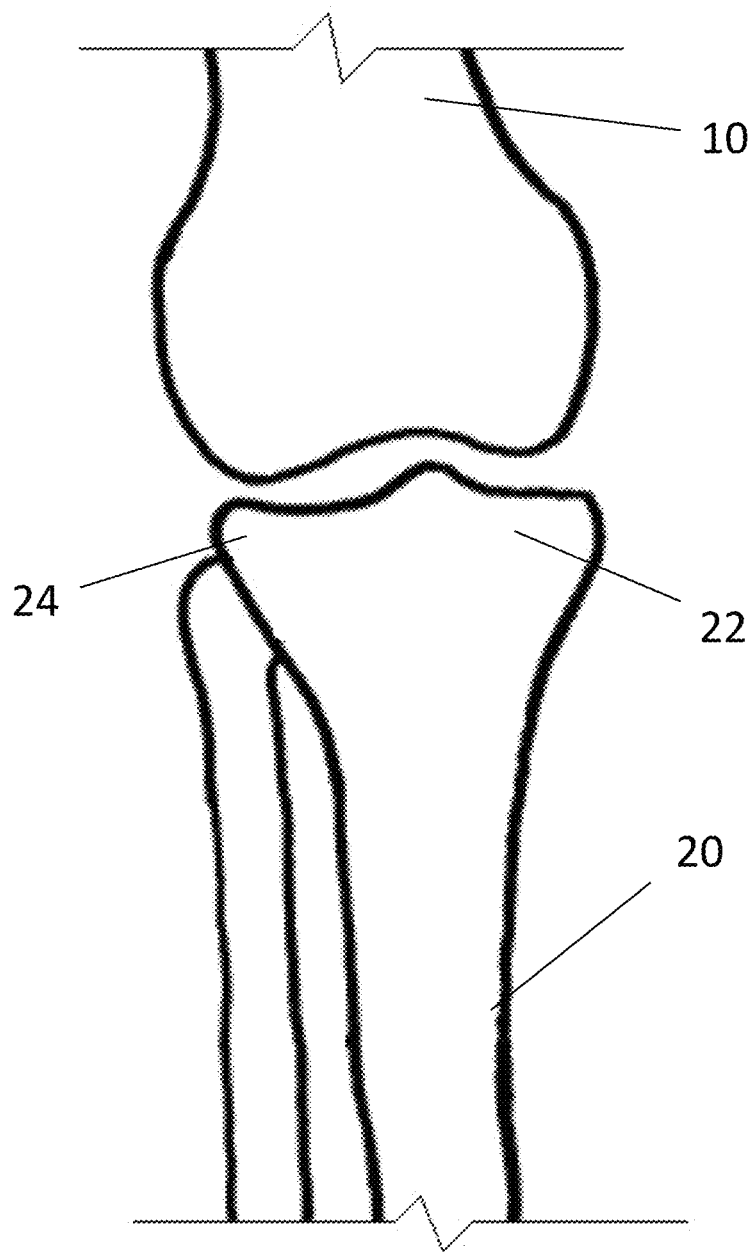
FIG. 1 is a highly schematic view of the bones of a knee joint.

The disclosure provided herein is generally directed to an alloprosthetic composite ("APC") implant, including a scaffold used in the implant. Although the disclosure is directed generally to a specific example of a tibial implant, it should be understood that the concepts provided herein may be applied to other APC implants, which are described in greater detail below. One example of an application of the APC implant described herein is a unicondylar or partial knee replacement. For example, FIG. 1 shows a highly schematic drawing of a knee joint including the distal portion of a femur 10 and the proximal portion of a tibia 20. The distal femur 10 includes a medial femoral condyle which articulates against a medial tibial condyle 22 and a lateral femoral condyle which articulates against a lateral tibial condyle 24. The distal femur 10 does not articulate directly against bone of the tibia 20, but rather against fibrocartilaginous tissue known as menisci that are positioned on top of the proximal tibia 20. Due to age, disease, trauma, or other causes, one or more of the articular surfaces of the tibia 20 may need to be replaced. For example, in a unicondylar knee replace, one of the tibial or femoral condyles may be replaced with a prosthetic implant. Although a unicondylar knee replacement may include replacement of both medial condyles of the femur 10 and tibia 20 (or both lateral condyles), the procedure for simplicity is described as solely replacement of the medial tibial condyle 22.

Figure 2:
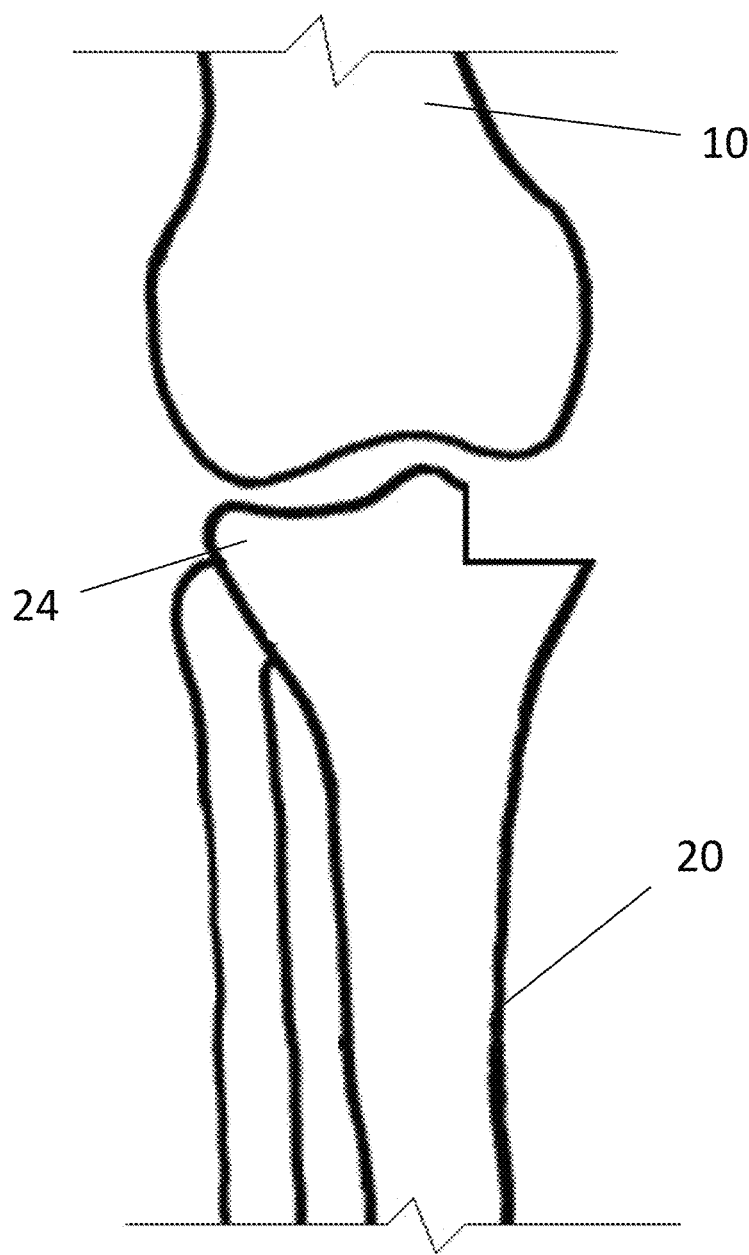
FIG. 2 is a highly schematic view of the bones of a knee joint during a unicondylar knee replacement.
Figure 3:
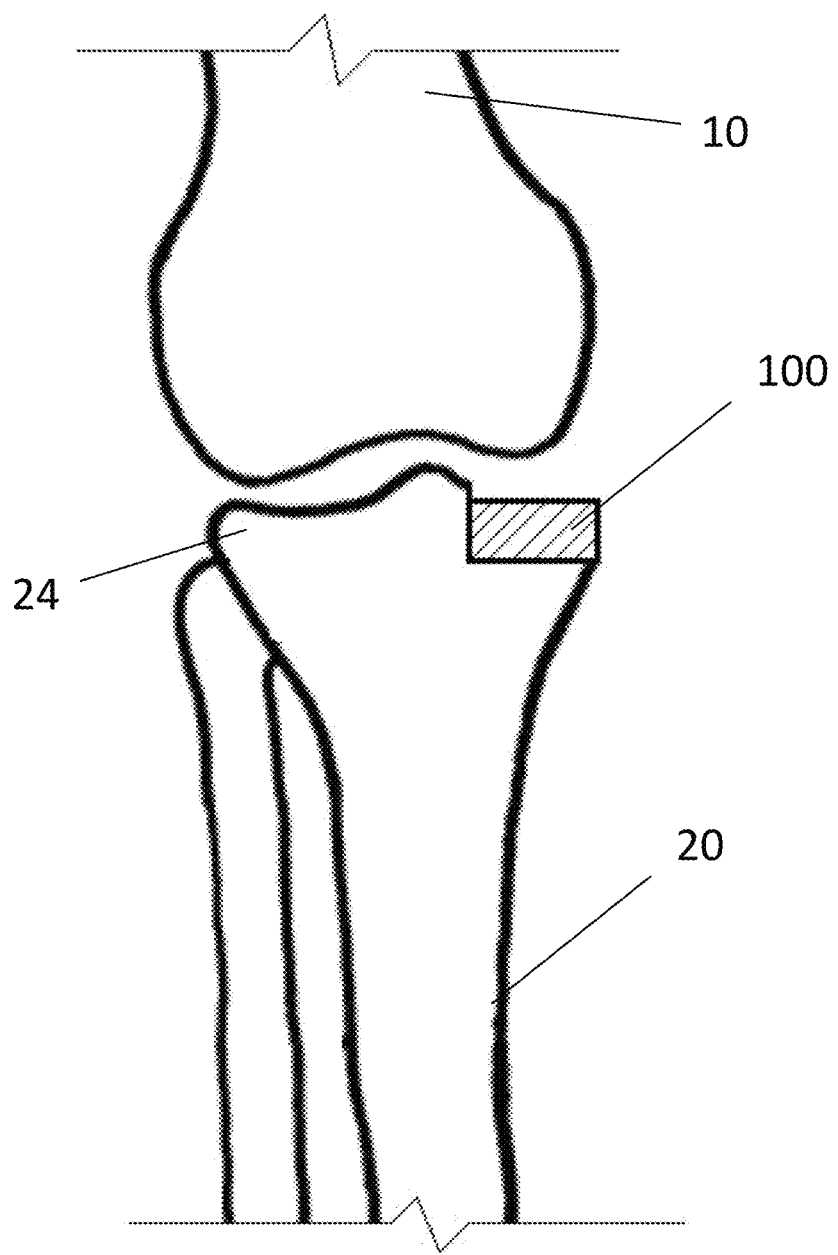
FIG. 3 is a highly schematic view of a prosthesis implanted into the knee joint of FIG. 2.

In such a unicondylar knee replacement, at least a portion of the medial tibial condyle 22, including the cartilage and subchondral bone, is removed, for example with a manually controlled or robotically controlled cutting tool, as shown in FIG. 2. Once the tibia 20 is properly prepared, an implant 100, such an APC implant formed according to the disclosure provided below, may be attached to the bone to restore normal or near-normal function to the joint, as shown in FIG. 3. It should be understood that implant 100 in FIG. 3 is represented as a block merely for ease of illustration, and, as explained in greater detail below, would be shaped to correspond to the particular anatomy of the patient as needed.

Figure 4A:
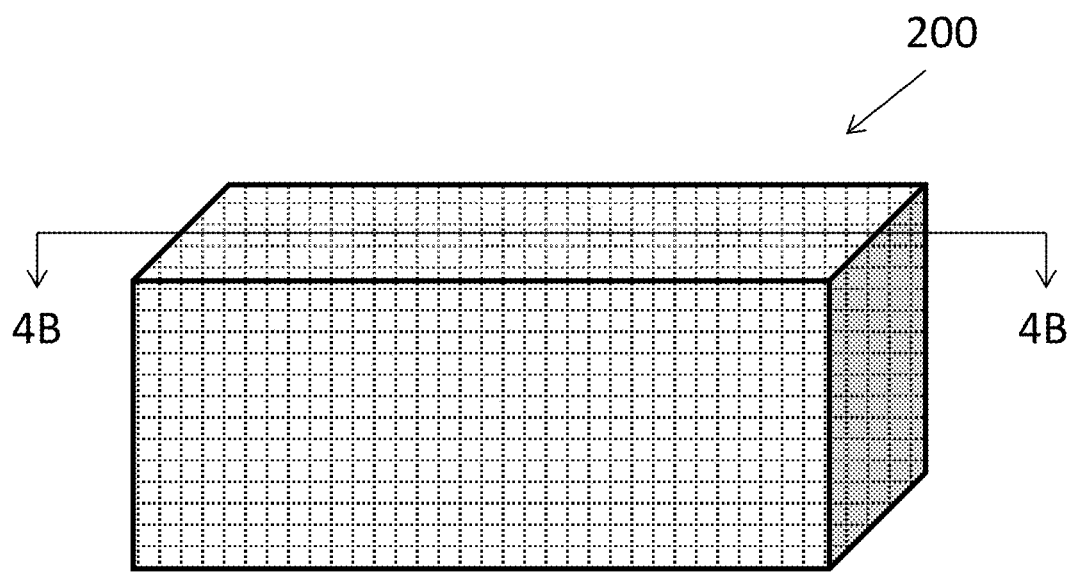
FIG. 4A is a perspective view of a scaffold of the prosthesis of FIG. 3.
Figure 4B:
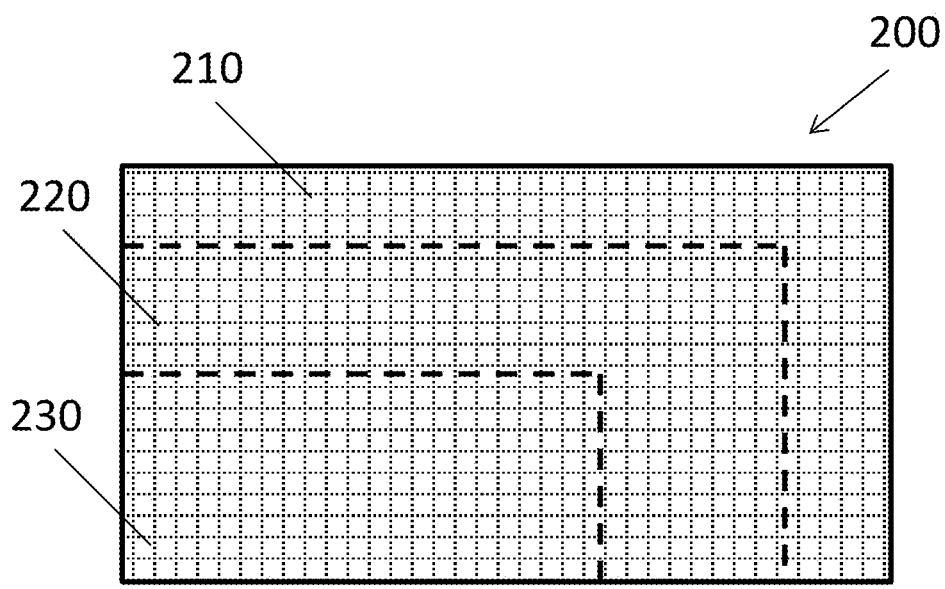
FIG. 4B is a cross-section of the scaffold of FIG. 4A taken along the lines 4B-4B of FIG. 4A.

FIGS. 4A-B are schematic illustrations of a scaffold 200 for use in creating an APC implant 100. In one example, scaffold 200 may be formed of a metallic material, such as titanium, formed into a porous three-dimensional structure. Preferably, scaffold 200 is formed via additive manufacturing, for example via 3D printing. One benefit of forming scaffold 200 via 3D printing is the ability to precisely control the structure, including the porosity, of the scaffold 200. For example, because part of the goal of using APC implant 100 is to mimic the native anatomy, it would be desirable to have at least a portion of scaffold 200 be filled with bone tissue that mimics the variable structure of the native bone. In particular, within a bone such as tibia 20, a transverse cross-section through tibia 20 would show that the outer cortical rim portions of tibia 20 have greater density compared to the center portions of tibia 20 which is generally referred to as cancellous (or spongy or trabecular) bone. It is possible to design scaffold 200 in such a way that bone that grows or is otherwise seeded into scaffold 200 grows in a way that mimics the variable density of the portions of the native bone being replaced by APC implant 100, as described in greater detail below.

It is possible to map the density of bone, including bone that is to be removed and bone adjacent the bone to be removed. Such a density map can be created by any suitable imaging means. For example, the portion of bone that will be replaced may be scanned and computed tomography used to determine a density profile of the bone. Such a density profile may be created, for example, by analyzing pixel brightness of portions of the scanned bone. It should be understood that other methods, including other imaging modalities, may provide suitable means to create a density map of the bone to be replaced. It should also be understood that it may be desirable to create density maps or profiles of surrounding bone, particularly if the bone being replaced is damaged or otherwise has an abnormal density profile which should not be replicated in APC implant 100.

FIG. 4A is a schematic illustration of a scaffold 200 of APC implant 100 intended for replacement of a medial tibia condyle 22. It should be understood that although scaffold 200 is illustrated as being rectangular, the actual shape of the scaffold 200 may be dictated by the requirements of the particular anatomy at issue. In the example of scaffold 200, the left side of scaffold 200 as shown in FIG. 4A is intended for placement adjacent the resected center of tibia 20, the bottom of scaffold 200 is intended for placement adjacent the resected bottom surface of medial tibia condyle 22, with the top, front, rear, and right sides of scaffold 200 forming defining the exterior faces of scaffold 200. As noted above, a bone density profile of tibia 20 would illustrate that the outer cortical rim has a relatively high the cartilage adapted to replace at least a portion of a joint surface of the joint density, with the density decreasing toward the center of tibia 20. It should also be understood that certain properties, structural features or voids may be provided in scaffold 200, whether or not each are provided by the imaging and/or modeling of natural anatomy described above. For example, the matrix of scaffold 200 is preferably designed to promote vascularization, such as through the inclusion of continuous channels throughout scaffold 200. Further, certain portions of scaffold 200 may have properties different from surrounding portions of the scaffold 200 to provide for particular functionality. For example, the matrix of scaffold 200 may be rougher, have increased texture, and be more vascular to provide for an enhanced ligament attachment site. This may correspond to natural features, such as bone fibers (or Sharpey's fibers) which may provide for attachment sites to bone. Using data corresponding to the bone density profile of tibia 20, scaffold 200 may be created, for example by 3D printing of titanium, so that the scaffold 200 has porosity that generally corresponds to the density profile of the bone being replaced (or, in the case the bone being replaced has an undesirable density profile, for example due to degeneration, the porosity profile of the scaffold would correspond to a desired density profile). It should be understood that other types of metals, as well as non-metals, including bioabsorbable materials or collagen, may individually or in combination form the scaffold 200. At least some inclusion of collagen in scaffold 200 may be preferable to help promote bone growth in and on the scaffold.

FIG. 4B shows a cross section of scaffold 200 taken along a longitudinal plane passing through the center of scaffold 200, as represented by line 4B-4B of FIG. 4A. As shown in FIG. 4B, scaffold 200 may include a variety of porosity zones 210, 220, 230 that generally correspond to the desired density profile of APC implant 100. In the illustrated example, porosity zone 210 may have relatively low porosity corresponding to relatively high density of cortical bone. Porosity zone 230 may have relatively high porosity corresponding to relatively low density of cancellous bone, with porosity zone 220 being intermediate. The amount of porosity may be determined, for example, by the amount of spacing between the metal, which may take a foam or lattice type of configuration. It should be understood that scaffold 200 need not include discrete porosity zones, but rather may include a gradient of porosities that correspond to the desired bone density of APC implant 100. Further, it should be understood that the shape of any porosity zones need not be rectangular or any other rigid shape, but may be dictated by the corresponding shapes of the desired bone density profile.

Figure 5:
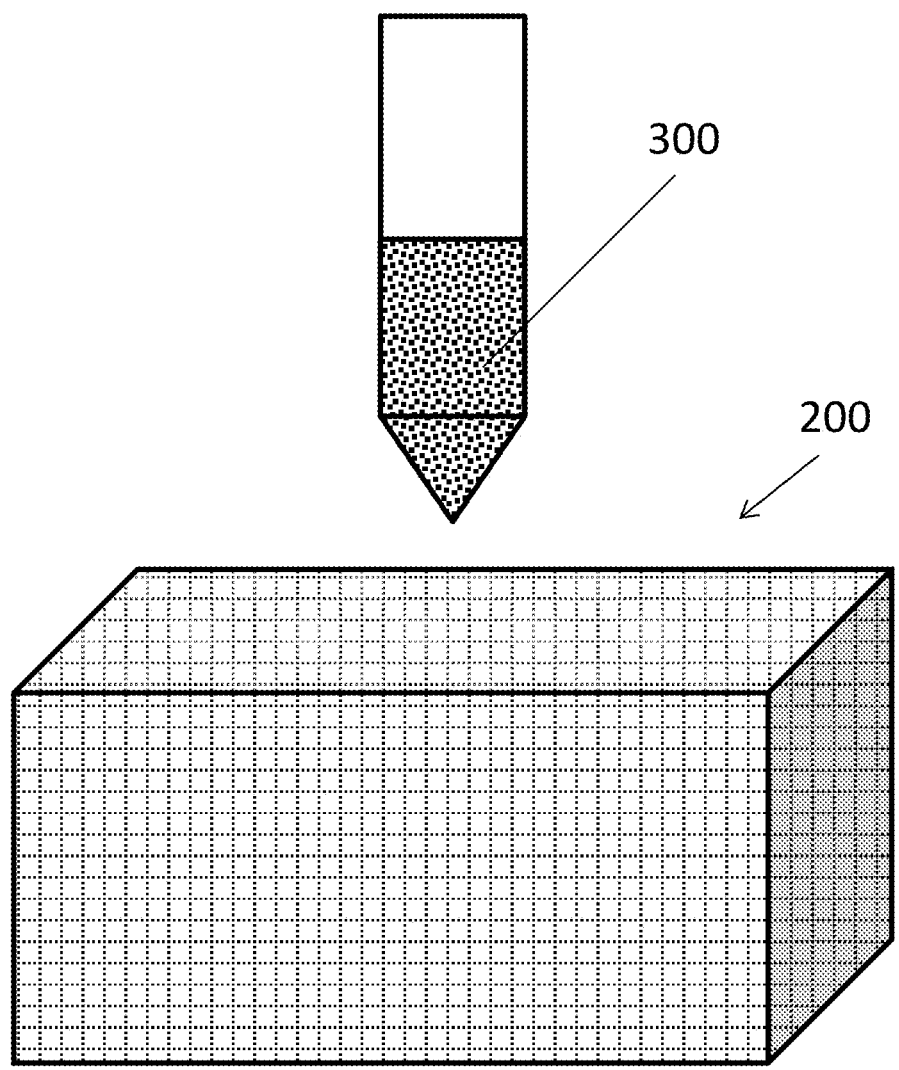
FIG. 5 is a perspective view of stem cells being introduced to the scaffold of FIG. 4A.

As shown in FIG. 5, stem cells 300 may be introduced or seeded into and/or onto scaffold 300. The harvesting and seeding of cells may be done by any suitable means, some of which are described in greater detail in U.S. Pat. No. 7,299,805, the contents of which are hereby incorporated by reference herein. For example, the cells used may be any suitable type of viable cells, preferably those that correspond to the native tissue being replaced. This may include, for example, chondrocytes (and/or chondroblasts), osteoblasts, fibrobalsts, and/or pluripotent cells or stem cells. Stem cells may be harvested, for example, from bone marrow or fetal cells. Although cells 300 are generally referred to as stem cells herein, it should be understood that any suitable type of cell or combination of cell types may be alternately used. Upon introduction into scaffold 200, stem cells 300 migrate through the scaffold 200, attaching to the metal that provides the structure of scaffold 200, with the stem cells 300 differentiating into bone cells over time. The attachment may be affected and controlled, for example, by the texture of the surface of scaffold 200 and the size of the pores within the scaffold 200. The use of collagen, as well as adding calcium and controlling the pH balance of the scaffold system may help promote bone growth. The differentiation into the desired cell type or types may be controlled, for example, by applying or exposing the cells to certain environmental conditions such as mechanical forces (static or dynamic), chemical stimuli (e.g. pH), and/or electromagnetic stimuli.

Figure 6:
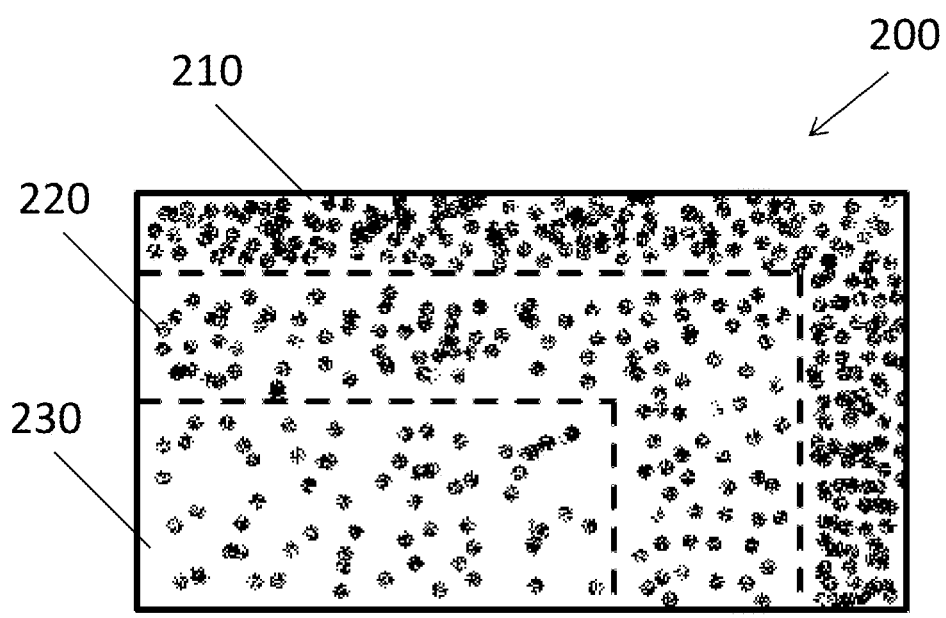
FIG. 6 is a cross-section of the scaffold of FIG. 4A with bone cells therein.

With the stem cells seeded into scaffold 200, the scaffold 200 may be placed inside an incubator. The incubator may include a nutrient rich medium that is flowed through the scaffold 200 to provide a desirable environment for the cells in the scaffold. The bone cells may grow and migrate through scaffold 200, with the bone growing more densely in the zones with low scaffold porosity, such as porosity zone 210, and less densely in the zones with high scaffold porosity, such as porosity zone 230, as shown in FIG. 6.

After the seeded bone cells have migrated and grown into scaffold 200, one or more layers of cartilage 240, 250 may then be grown on top of the bone. For example, a first deep layer 240 of cartilage may be grown on top of the relatively dense bone in porosity zone 210, and a gliding layer 250 may be grown on top of the deep layer 240. Gliding layer 250 may provide a surface for articulation with a bone of a corresponding joint, such as a femoral condyle. The growth of the cartilage layers 240, 250 may also be assisted with the use of an incubator, with the cartilage growth taking place over a period of up to eight weeks, for example. The differentiation between cartilage layers 240, 250 may be based, at least in part, on difference within the scaffold 200 upon which the cartilage grows. Although the cells are described as being seeded and incubated prior to implant, it should be understood that the scaffold 200 may first be implanted into the patient with the cells being seeded into the scaffold 200 intraoperatively.

Figure 7:
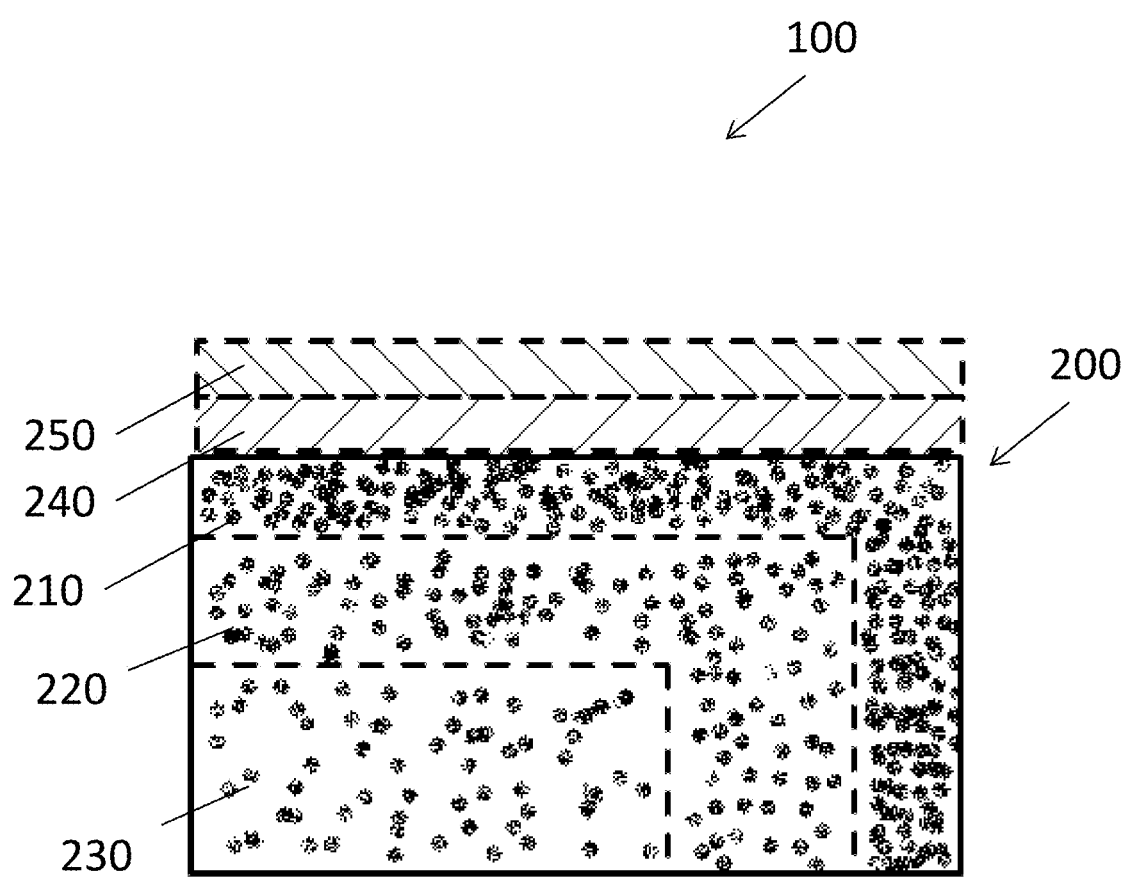
FIG. 7 is a cross-section of prosthesis of FIG. 3 with layers of cartilage.
Figure 8A:
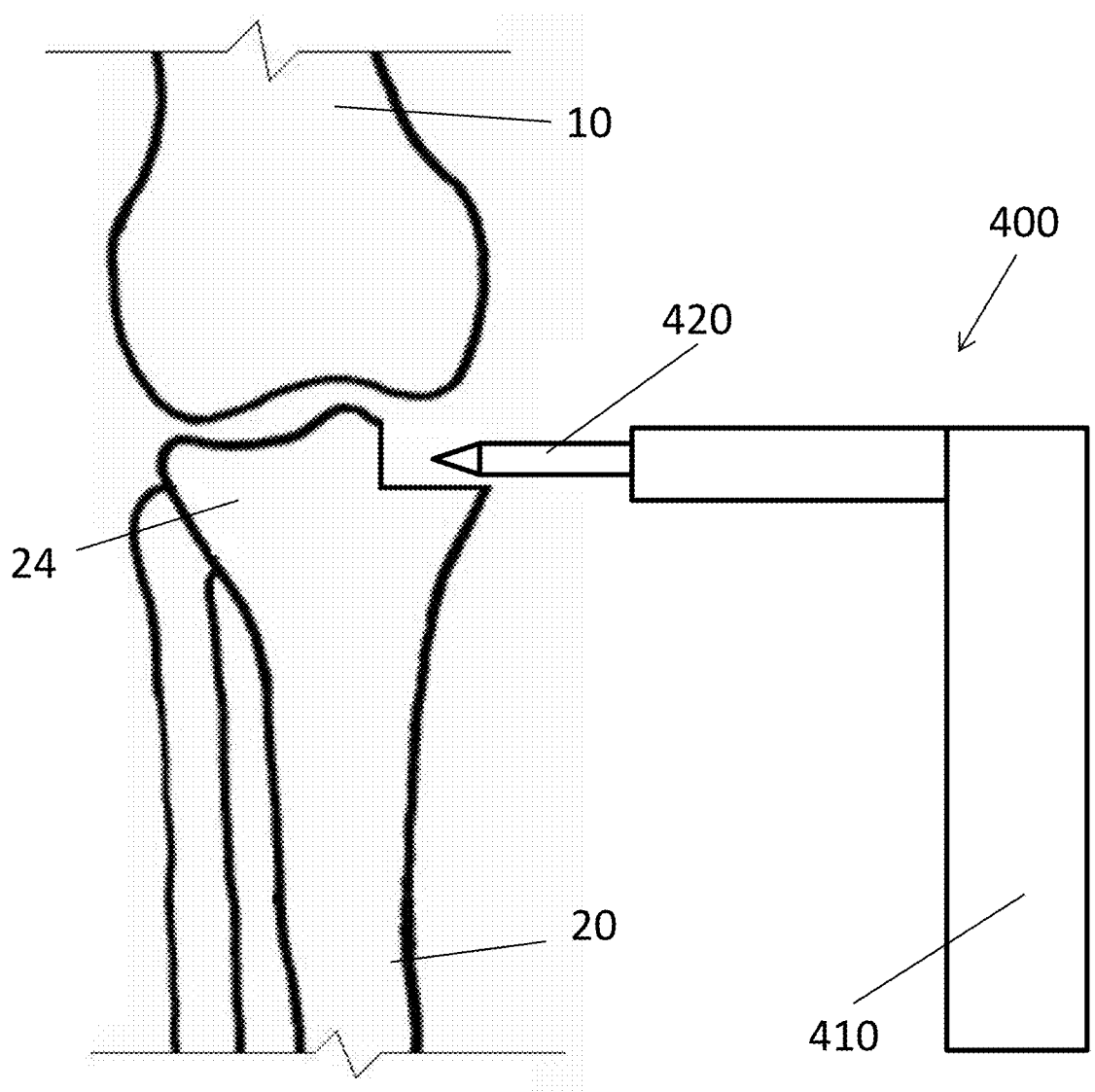
FIG. 8A is schematic view of a robotic device resecting a bone.
Figure 8B:
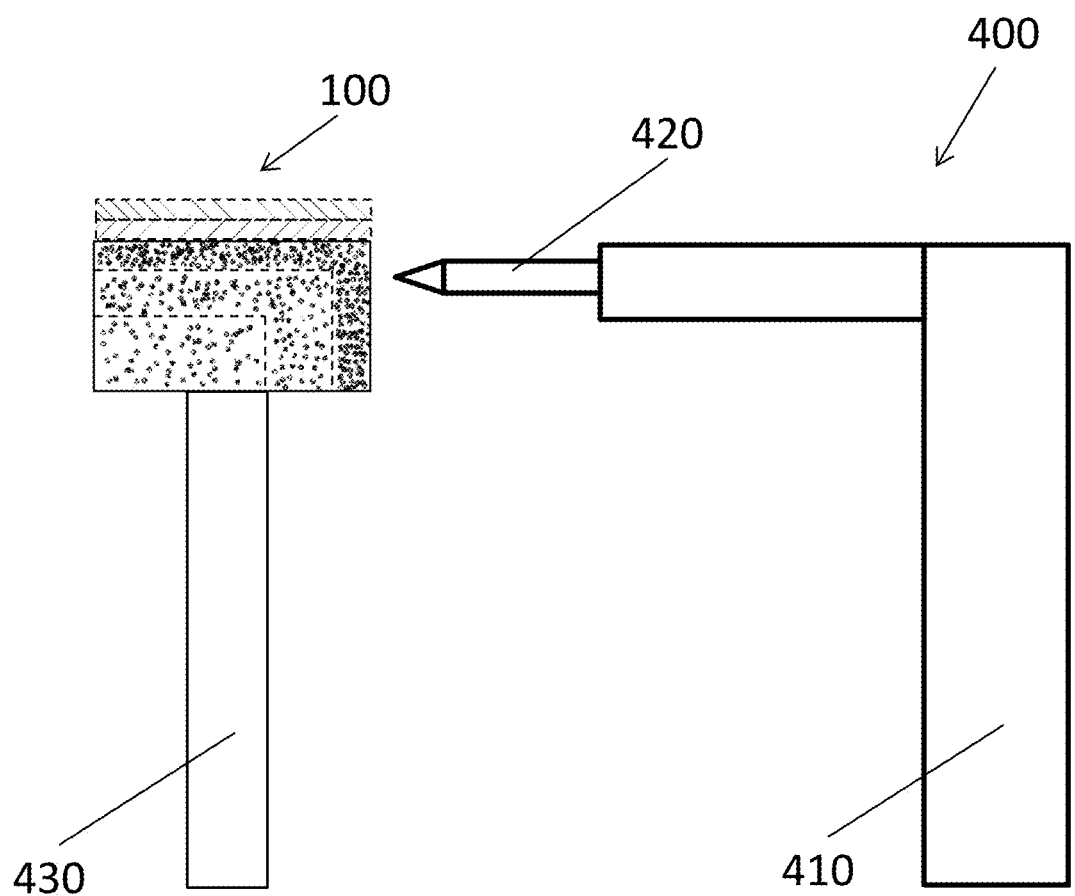
FIG. 8B is a schematic view of the robotic device of FIG. 8A shaping the prosthetic implant of FIG. 7.

The implant 100 with both bone grown throughout the scaffold 200 and cartilage layers 240, 250 grown on top of the bone is shown in FIG. 7. At this point, the implant 100 may be ready or near-ready for implantation. For example, in a unicondylar knee replacement procedure, implant 100 may be provided in the operating room where the knee replacement is to take place. Preferably, the medial tibial condyle 22 is resected according to an operative plan with the use of an autonomous or semi-autonomous robotic system, such as the robotic system described in greater detail in U.S. Pat. No. 8,287,522, the disclosure of which is hereby incorporated by reference herein. For example, as shown in FIG. 8A, a robotic device 400 with a robotic arm 410 and a cutting tool end effector 420 may resect medial tibial condyle 22 according to a plan in a computer controlling robotic device 400. Based on the particular geometry of the resected native bone, robotic device 400 may be used to shape implant 100 to have a corresponding fit to the implant site. Implant 100 may be fixed to a stand 430 or other device to secure the implant 100 as the end effector 420 of robotic device 400 customizes the shape of implant 100.

Once shaped, implant 100 may be press-fit, packed, or otherwise implanted into the implant site. The robotic device 400 may also assist in the step of positioning the implant 100 onto the native bone, for example with the aid of a navigation system and/or sensors to position the implant 100 in the desired three-dimensional position with respect to the tibia 20. Any known type of external hardware, such as fixation screws or pegs, may be used to facilitate the initial connection of the implant 100 to the native anatomy. As noted previously, scaffold 200 preferably includes a density profile that mimics or otherwise corresponds to the bone density profile of the native bone that will be positioned adjacent the implant 100. The native bone will grow into the scaffold 200, with the matching density profiles resulting in better bone ingrowth compared to other implants. For example, it has been found that, for fresh allograft and frozen osteochondral graft, it is difficult to get native bone to grow into the implant surface. However, bone consistently grows to surface of metallic porous scaffold 200, particularly with its three-dimensional surface. Furthermore, matching density profiles between the native bone and the scaffold 200 further encourages bony ingrowth into the scaffold 200.

It should be understood that the fabrication of scaffold 200 may be complicated. One alternative option in creating the scaffold is through use of the body's own scaffold as a guide. For example, a user may start with a body portion (e.g. a tibia portion of a knee joint) and repeatedly apply aldehyde to remove tissue, bone, hydroxyapatite, and/or selenium material, leaving only collagen and the scaffold behind. The three-dimensional structure and geometry of the remaining cartilage and scaffold can then be mapped. For example, lasers or other suitable devices may scan or otherwise map the scaffold and cartilage and to store the structure in computer memory so that the structure could be easily reproduced, for example via additive manufacturing. Rather than mapping, a negative mold of the scaffold could be created so that the scaffold could be reproduced with the mold. The scaffold could be created from metal as described above, or alternately created directly with tissue. For example, a 3D printer could be used to build a scaffold directly with bone cells and/or collagen without the need to impregnate a metal scaffold with cells. In other embodiments, the scaffold 200 may be produced in a manner described in U.S. Pat. No. 8,992,703, the disclosure of which is hereby incorporated by reference herein. For example, the method of forming the three-dimensional scaffold 200 may include building the shape by laser melting powdered titanium and titanium alloys, stainless steel, cobalt chrome alloys, tantalum or niobium using a continuous or pulsed laser beam. Individual layers of metal may be scanned using a laser. The laser may be a continuous wave or pulsed laser beam. Each layer or portion of a layer may be scanned to create a portion of a plurality of predetermined unit cells. Successive layers may be deposited onto previous layers and also may be scanned. The scanning and depositing of successive layers may continue the building process of the predetermined unit cells. Continuing the building process may refer not only to a continuation of a unit cell from a previous layer but also a beginning of a new unit cell as well as the completion of a unit cell.

Although described above in the context of replacing a joint, and particularly a tibial condyle of a knee joint, the concepts provided above may extend to creating other alloprosthetic composite prostheses. For example, prostheses with scaffolds similar to those described above, with or without cartilage, may be implemented to replace segmental defects of bone after trauma, for arthrodesis, or for correcting leg length discrepancies. Other potential uses include for spinal fusion, in which the scaffold facilitates the fusion rather than a more typical prosthetic cage device. When used in the spine, the prosthesis may facilitate soft tissue graft, for example to replace the annulus fibrosus and nucleus pulposus with ingrowth into the vertebral endplates. The scaffolds described above could also be used for pure tissue grafts, for example when a rotator cuff is missing. Such an implant could be formed from a tissue scaffold, rather than a metal or bone scaffold, with tissue ingrowth into the tissue scaffold.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of implanting an alloprosthetic composite implant including an implant scaffold, the method comprising:
   determining a bone density profile of a bone of a patient to be contacted by the scaffold;
   forming the scaffold to have a pore density profile, wherein the pore density profile of the scaffold is formed based on the determined bone density profile of the bone of the patient;
   seeding a plurality of viable cells into the scaffold;
   incubating the scaffold including the plurality of viable cells to grow bone throughout the scaffold;
   after growing the bone throughout the scaffold, growing at least one layer of cartilage on top of the grown bone to produce the alloprosthetic composite implant having a first shape;
   robotically resecting native bone of a patient to have a particular geometry; and
   after growing the at least one layer of cartilage on top of the grown bone, fixing the alloprosthetic composite implant having the first shape to a stand, and intraoperatively robotically machining the alloprosthetic composite implant from the first shape into a second shape corresponding to the particular geometry while the alloprosthetic composite implant is fixed to the stand, the second shape being different than the first shape; and
   implanting the alloprosthetic composite implant having the second shape into patient adjacent the resected native bone of the patient,
   wherein a portion of the scaffold intended to contact the native bone is formed with a pore density profile based on the determined bone density profile of the bone of the patient to be contacted by the scaffold.

2. The method of claim 1, wherein the step of forming the scaffold is performed by additive manufacturing.

3. The method of claim 2, wherein the additive manufacturing is 3-D printing.

4. The method of claim 1, wherein the step of robotically resecting native bone of the patient includes forming a first interlocking shape in the native bone and the step of robotically machining the alloprosthetic composite implant includes forming a second interlocking shape in the alloprosthetic composite implant having a complementary shape to the first interlocking shape.

5. The method of claim 1, wherein the formed scaffold includes an inner portion adapted to contact native bone of the patient, and an outer portion opposite the inner portion, a scaffold density of the outer portion being greater than a scaffold density of the inner portion.

6. The method of claim 5, wherein the outer portion of the scaffold is formed with a lower pore density than the inner portion of the scaffold.

7. The method of claim 6, wherein the pore density of the outer portion of the scaffold is based on a density of a cortical section of the bone of the patient.

8. The method of claim 6, wherein the pore density of the inner portion of the scaffold is based on a density of a cancellous section of the bone of the patient.

9. The method of claim 1, wherein the scaffold is formed from metal.

10. The method of claim 9, wherein the metal is titanium.

11. The method of claim 1, wherein the scaffold is formed of a bioabsorbable material.

12. The method of claim 1, wherein seeding the plurality of viable cells into the scaffold includes seeding osteoblasts into the scaffold.

13. The method of claim 1, wherein seeding the plurality of viable cells into the scaffold includes seeding pluripotent cells into the scaffold.

14. The method of claim 1, wherein growing the at least one layer of cartilage on top of the grown bone includes forming a first inner layer of cartilage on the scaffold prior to robotically machining the alloprosthetic composite implant.

15. The method of claim 14, further wherein growing the at least one layer of cartilage on top of the grown bone includes forming a second layer of cartilage on the first layer of cartilage prior to robotically machining the alloprosthetic composite implant.

16. The method of claim 1, wherein incubating the scaffold includes incubating the scaffold in a nutrient rich medium.

17. The method of claim 1, wherein the scaffold is formed of collagen.

* * * * *